(12) United States Patent
Roschenthaler et al.

(10) Patent No.: US 9,472,831 B2
(45) Date of Patent: Oct. 18, 2016

(54) LITHIUM-2-METHOXY-1,1,2,2-TETRA-FLUORO-ETHANESULFONATE AND USE THEREOF AS CONDUCTIVE SALT IN LITHIUM-BASED ENERGY ACCUMULATORS

(75) Inventors: Gerd-Volker Roschenthaler, Bremen (DE); Martin Winter, Munster (DE); Katja Vlasov, Mannheim (DE); Nataliya Kalinovich, Bremen (DE); Christian Schreiner, Biberbach (DE); Raphael Wilhelm Schmitz, Munster (DE); Romek Ansgar Muller, Bad Bentheim (DE); Rene Schmitz, Mannheim (DE); Alexandra Lex-Balducci, Munster (DE); Miriam Kunze, St. Andreasberg (DE)

(73) Assignees: Westfalische Wilhelms Universitat Munster, Munster (DE); Jacobs University Bremen GGMBH, Bremen (DE)

( * ) Notice: Subject to any disclaimer, the term of this patent is extended or adjusted under 35 U.S.C. 154(b) by 300 days.

(21) Appl. No.: 14/234,767

(22) PCT Filed: Jul. 25, 2012

(86) PCT No.: PCT/EP2012/064584
§ 371 (c)(1),
(2), (4) Date: Mar. 28, 2014

(87) PCT Pub. No.: WO2013/014180
PCT Pub. Date: Jan. 31, 2013

(65) Prior Publication Data
US 2014/0377667 A1 Dec. 25, 2014

(30) Foreign Application Priority Data
Jul. 26, 2011 (DE) ........................ 10 2011 052 156

(51) Int. Cl.
*H01M 10/0569* (2010.01)
*H01M 10/0568* (2010.01)
*C07C 309/10* (2006.01)
*H01G 11/62* (2013.01)
*H01M 10/052* (2010.01)
*H01G 11/06* (2013.01)

(52) U.S. Cl.
CPC ........ *H01M 10/0568* (2013.01); *C07C 309/10* (2013.01); *H01G 11/62* (2013.01); *H01M 10/052* (2013.01); *H01M 10/0569* (2013.01); *H01G 11/06* (2013.01); *H01M 2300/0037* (2013.01); *Y02E 60/122* (2013.01); *Y02E 60/13* (2013.01)

(58) Field of Classification Search
CPC .... C07C 309/10; H01G 11/62; H01G 11/06; H01M 10/052; H01M 10/0568; H01M 10/0569; H01M 2300/0037; Y02E 60/122; Y02E 60/13
See application file for complete search history.

(56) References Cited

U.S. PATENT DOCUMENTS

| 6,506,516 B1 | 1/2003 | Wietelmann et al. |
| 2002/0197558 A1 | 12/2002 | Ferreira et al. |

FOREIGN PATENT DOCUMENTS

| DE | 19829030 C1 | 10/1999 |
| EP | 1026152 A1 | 8/2000 |
| EP | 1220344 A2 | 7/2002 |
| EP | 1095071 B1 | 6/2004 |
| EP | 1598896 A1 | 11/2005 |
| JP | 1092222 A | 4/1998 |
| WO | 0178183 A1 | 10/2001 |
| WO | 2012084066 A1 | 6/2012 |

OTHER PUBLICATIONS

Paillard, et al: "Electrochemical invesiation of polymer electrolytes based on lithium 2-(phenylsufanyl)-1,1,2,2- tetrafluoro-ethansulfonate"; Electrochimica Acta, Elsevier Science Publishers, Barking, GB, Bd. 53, Nr. 4, Oct. 30, 2007, pp. 1439-1443.
Arvai, et al, "New aryl-containing fluorinated sulfonic acids and their ammonium salts, useful as electrolyes for fuel cells or ionic liquids"; Journal of Fluorine Chemistry, Elsevier,Bd. 129, Nr. 10, Oct. 1, 2008, pp. 1029-1035.
International Search Report (Translated) for PCT/EP2012/064584; dated Sep. 4, 2012; 3 pages.
PCT International Preliminary Report on Patentability for International application No. PCT/EP2012/064584, dated Jan. 28, 2014, 10 pages.

*Primary Examiner* — Muhammad Siddiquee
(74) *Attorney, Agent, or Firm* — Reising Ethington P.C.

(57) ABSTRACT

The invention relates to lithium-2-methoxy-1,1,2,2-tetra-fluoro-ethanesulfonate, to the use thereof as conductive salt in lithium-based energy accumulators, and ionic liquids comprising 2-methoxy-1,1,2,2-tetrafluoro-ethanesulfonate as an anion.

9 Claims, 6 Drawing Sheets

LITHIUM-2-METHOXY-1,1,2,2-TETRA-FLUORO-ETHANESULFONATE AND USE THEREOF AS CONDUCTIVE SALT IN LITHIUM-BASED ENERGY ACCUMULATORS

TECHNICAL FIELD

The invention relates to lithium-2-methoxy-1,1,2,2-tetrafluoro-ethanesulfonate as well as the use of lithium-2-methoxy-1,1,2,2-tetrafluoro-ethanesulfonate as a conductive salt in lithium-based energy accumulators. The invention also relates to ionic liquids, including 2-methoxy-1,1,2,2-tetrafluoro-ethanesulfonate as an anion.

BACKGROUND

Lithium ion technology is the leading technology in the area of rechargeable battery accumulator systems for portable electronics. Lithium ion batteries are used as storage systems in mobile telephones, camcorders, laptops and for some time even in battery-powered tools. The next step to aim for is the use of lithium ion batteries in larger systems such as in automobiles or as stationary energy accumulators for renewable energy. Because of their high cell voltage, superior energy and power density as well as their low self-discharge, lithium ion batteries have a high potential for these applications. However, commercially available batteries do not fulfill the safety requirements for large systems. The thermal and chemical stability of the liquid electrolytes used plays an important part in this. Since heat arises with the discharge of lithium ion batteries, sufficient thermal stability of the electrolytes used is typically necessary for their use, especially for large systems with several hundred to a thousand kilowatt-hours of stored power.

Presently, lithium hexafluorophosphate ($LiPF_6$) is used as a conductive salt in commercially available batteries. Lithium hexafluorophosphate has relatively high conductivity and is capable of forming a passivation layer, the so-called solid electrolyte interphase (SEI), on graphite electrodes. Lithium hexafluorophosphate, however, has considerable disadvantages because of its low thermal and chemical stability. It is known that $LiPF_6$ reacts with traces of water and other protic compounds such as alcohol, which are not always completely avoidable in lithium batteries and occur, for example, in solvents in the ppm-area, and forms the toxic compounds $POF_3$ and HF, which accelerate the disintegration of the spinels $Li_xMn_2O_4$ used as cathode materials as well as the degradation of the passivation layers both on the anode and the cathode. This reaction is accelerated by moderately elevated temperatures. This makes for a rapid loss of cell capacity that results in a shortened lifetime of the cell.

Thus, there are intensive efforts to develop alternative lithium salts that can replace $LiPF_6$ as a conductive salt. Lithium salts developed in recent years are often complex boric and phosphoric anions with non-aromatic chelating agents like oxalate, for example lithium bis(oxalato)borate (LiBOB) disclosed in DE 198 29 030 C1. However, there is a disadvantage in that bis(oxalato)borate has only slight solubility in carbonates used as solvents in electrolytes. LiBOB-based electrolytes also have lower conductivity and higher viscosity in comparison with $LiPF_6$. In particular, bis(oxalato)borate electrolytes have only slight conductivity at low temperatures. Moreover, the production of bis(oxalato)borate of sufficient purity is expensive, since the contamination with oxalate and carboxylate at elevated temperatures leads to the escape of gases from the cells. A further disadvantage of the use of lithium bis(oxalato)borate is that an overly strong SEI is formed by which cell resistance is increased.

In spite of a multitude of salts and solvents, still no suitable replacement for $LiPF_6$ as a conductive salt in carbonate mixtures has been found. Thus, there is a need of alternative lithium salts.

SUMMARY

One object of the present disclosure is to provide a compound that overcomes at least one of the abovementioned disadvantages of the prior art. In particular, one object is to provide a lithium compound in carbonate mixtures suitable as a conductive salt.

In one embodiment, this object is achieved by the compound lithium-2-methoxy-1,1,2,2-tetrafluoro-ethanesulfonate. Lithium-2-methoxy-1,1,2,2-tetrafluoro-ethanesulfonate is also designated as lithium-1,1,2,2-tetrafluor-2-methoxy-ethanesulfonate.

Surprisingly, it was found that electrolytes which contain the compound lithium-2-methoxy-1,1,2,2-tetrafluoro-ethanesulfonate as the lithium salt show no HF development even at temperatures of 95° C. In thermal aging experiments it was established that for these electrolytes, even after storing at 95° C. for two weeks, in contrast to $LiPF_6$-based electrolytes, no HF development was visible in nuclear magnetic resonance (NMR) spectra. It was also established that with electrolytes containing lithium-2-methoxy-1,1,2,2-tetrafluoro-ethanesulfonate after storing at 95° C. for two weeks, in contrast to electrolytes containing $LiPF_6$, no carbonate-decomposition products in electrolytes were noticeable. Good thermal stability is one advantage of lithium-2-methoxy-1,1,2,2-tetrafluoro-ethanesulfonate in some embodiments. This enables an extended temperature range for the use of lithium-2-methoxy-1,1,2,2-tetrafluoro-ethanesulfonate as a lithium conductive salt. Likewise, cells using lithium-2-methoxy-1,1,2,2-tetrafluoro-ethanesulfonate as a conductive show an excellent cycle stability.

Furthermore, lithium-2-methoxy-1,1,2,2-tetrafluoro-ethanesulfonate shows good electrochemical stability as well. Thus, in a mixture of ethylene carbonate (EC) and diethyl carbonate (DEC) lithium-2-methoxy-1,1,2,2-tetrafluoro-ethanesulfonate shows an anodic stability of 5.6 V. This value is at the same level as that which is aimed for in carbonate mixtures with $LiPF_6$, 5.9 V, and is sufficient for use with high voltage cathode materials. In particular, corrosion measurements show that lithium-2-methoxy-1,1,2,2-tetrafluoro-ethanesulfonate exhibits no corrosion of the aluminum used on the cathode side as current collector, but forms a protective layer on aluminum like $LiPF_6$.

Besides the positive property of showing no HF development, lithium-2-methoxy-1,1,2,2-tetrafluoro-ethanesulfonate has a good lithium-ion conductivity, high electrochemical stability and good SEI film-forming properties. Additionally, lithium-2-methoxy-1,1,2,2-tetrafluoro-ethanesulfonate is not flammable and is usable in a wide temperature range.

In contrast to $LiPF_6$ electrolytes, considerable improvement of reliability can be provided by avoidance of HF development even in the presence of a greater quantities of water with lithium-2-methoxy-1,1,2,2-tetrafluoro-ethanesulfonate.

Lithium-2-methoxy-1,1,2,2-tetrafluoro-ethanesulfonate may show the advantage of developing no HF even at elevated temperatures, and less toxicity of the combustion products than LiPF$_6$. This enables a broader temperature range in the use, for example, of lithium-ion accumulators at comparable output. Therefore, lithium-2-methoxy-1,1,2,2-tetrafluoro-ethanesulfonate is usable as a conductive salt for commercial lithium ion batteries.

Another subject matter of the present disclosure relates to the use of lithium-2-methoxy-1,1,2,2-tetrafluoro-ethanesulfonate in lithium-based energy accumulators, particularly as a conductive salt. Primary and secondary lithium-based energy accumulators are preferably selected from the group including lithium batteries, lithium ion batteries, lithium ion accumulators, lithium polymer batteries and/or lithium ion condensers. Lithium-2-methoxy-1,1,2,2-tetrafluoro-ethanesulfonate is particularly suited as a conductive salt for a lithium ion battery or a lithium ion accumulator. Lithium-2-methoxy-1,1,2,2-tetrafluoro-ethanesulfonate is also suitable as a conductive salt for lithium-based energy accumulators, which are indicated as a further development of lithium ion accumulators, preferably selected from the group including lithium titanium accumulators, lithium air accumulators, lithium manganese accumulators, lithium iron phosphate accumulators, lithium iron manganese phosphate accumulators, lithium iron yttrium phosphate accumulators, lithium sulfur accumulators, lithium nickel cobalt manganese oxide accumulators, lithium nickel cobalt aluminum oxide accumulators and tin sulfur lithium accumulators.

Charge transfer in electrochemical energy accumulators occurs through an electrolyte. A liquid electrolyte is commonly formed essentially from a lithium conductive salt dissolved in a solvent.

A further subject matter of the disclosure relates to an electrolyte for a lithium-based energy accumulator including lithium-2-methoxy-1,1,2,2-tetrafluoro-ethanesulfonate. Lithium-based energy accumulators including lithium-2-methoxy-1,1,2,2-tetrafluoro-ethanesulfonate as a conductive salt may have the advantage of good thermal and electrochemical stability.

Preferably, the electrolyte comprises an aprotic solvent, an ionic liquid and/or polymer matrix. Preferably, an electrolyte comprises an aprotic solvent and lithium-2-methoxy-1,1,2,2-tetrafluoro-ethanesulfonate. It was determined that lithium-2-methoxy-1,1,2,2-tetrafluoro-ethanesulfonate has good solubility in aprotic solvents, particularly cyclic or linear carbonates. This enables the use of lithium-2-methoxy-1,1,2,2-tetrafluoro-ethanesulfonate in the liquid electrolytes used in commercial lithium ion batteries.

In preferred embodiments, the aprotic solvent is selected from the group including ethylene carbonate, propylene carbonate, diethyl carbonate, dimethyl carbonate, ethyl methyl carbonate, acetonitrile, glutaronitrile, adiponitrile, pimelonitrile, γ-butyrolactone, γ-valerolactone, dimethoxyethane, 1,3-dioxalane, methyl acetate and/or mixtures thereof. Cyclic carbonates are preferred such as ethylene carbonate or propylene carbonate, and/or linear carbonates such as diethyl carbonate, dimethyl carbonate or ethyl methyl carbonate. Preferably, the aprotic solvent is selected from the group including ethylene carbonate, diethyl carbonate, dimethyl carbonate and/or their mixtures.

Preferable are mixtures of ethylene carbonate and at least one other aprotic solvent, particularly preferred, with diethyl carbonate or dimethyl carbonate. In preferred embodiments, the aprotic solvent is a mixture of ethylene carbonate and at least one other aprotic solvent, preferably diethyl carbonate. Preferably, the ratio of ethylene carbonate and the at least one other solvent, preferably diethyl carbonate, lies in the range of 1:9 to 9:1, more preferably in the range of 3:7 to 7:3, most preferably in the range of (i) 3:7 to 1:1. If not stated otherwise, this refers to the ratio of the parts by weight of the solvents.

In a solvent mixture of ethylene carbonate and diethyl carbonate (EC:DEC) in the ratio 1:1, the greatest conductivity can be attained to advantage in a temperature range of −20° C. to +60° C.

Ionic liquids have proven themselves to be promising electrolyte materials since they combine a high thermal and electrochemical stability with a high ionic conductivity. This may be advantageous for use with lithium-2-methoxy-1,1,2,2-tetrafluoro-ethanesulfonate.

Preferred ionic fluids comprise a cation selected from the group including 1-ethyl-3-methylimidazolium (EMI$^+$), 1-2-dimethyl-3propylimidazolium (DMPI$^+$), 1,2-diethyl-3,5-dimethylimidazolium(DEDMI$^+$), trimethyl-n-hexylammonium (TMHA$^+$), N-alkyl-N-methylpyrrolidinium (PYR$_{1R}^+$), N-alkyl-N-methyl piperidinium (PIP$_{1R}^+$) and/or N-alkyl-N-methylmorpholinium (MORP$_{1R}^+$) and an anion selected from the group including bis(trifluoromethanesulfonyl)imide (TFSI$^-$), bis(pentafluoroethane sulfonyl)imide (BETI$^-$), bis(fluorosulfonyl)imide (FSI$^-$), 2,2,2-trifluoro-N-(trifluoromethane sulfonyl)acetamide (TSAC$^-$), tetrafluoroborate (BF$_4^-$), pentafluoroethane trifluoroborate (C$_2$F$_6$BF$_3^-$), hexafluorophosphate (PF$_6^-$) and/or tri(pentafluoroethane) trifluorophosphate ((C$_2$F$_5$)$_3$PF$_3^-$). Preferred N-alkyl-N-methylpyrrolidinium (PYR$_{1R}^+$) cations are selected from the group including N-butyl-N-methylpyrrolidinium (PYR$_{14}^+$), and/or N-methyl-N-propylpyrrolidinium (PYR$_{13}^+$). Preferred ionic fluids are selected from the group including N-butyl-N-methylpyrrolidinium bis(trifluoromethanesulfonyl)imide (PYR$_{14}$TSFI) and/or N-methyl-N-propylpyrrolidinium bis(trifluoromethanesulfonyl)imide (PYR$_{13}$TSFI).

Other suitable electrolyte materials are polymer electrolytes in which the polymer electrolyte can be present as a gel polymer electrolyte or solid polymer electrolyte.

Solid polyelectrolytes have good properties relating to the requirements of future accumulator generations. They enable a solventless structure that is easy to produce and varied in form. Moreover, the energy density can be increased because the three-layer structure, electrolyte-separator-electrolyte is not applicable, so that only a thin polymer foil between the electrodes is necessary. Solid electrolytes as a rule are chemically and electrochemically stable towards electrode materials and do not escape further from the cell. Gel polymer electrolytes mostly comprise an aprotic solvent and a polymer matrix.

Preferred polymers for solid polymer electrolytes and gel polymer electrolytes are selected from the group including homopolymers or copylmers of polyethylene oxide (PEO), polypropylene oxide (PPO), polyvinylidene fluoride (PvdF), polyvinylidene fluoride hexafluoropropylene (PvdF-HFP), polyacrylonitrile (PAN), polymethyl methacrylate (PMMA), polyethyl methacrylate (PEMA), polyvinyl acetate (PVAc), polyvinyl chloride (PVC), polyphophazene, polysiloxane, polyvinyl alcohol (PVA) and/or homopolymers and (block polymer) copolymers, including side chains selected from the group of ethylene oxide, propylene oxide, acrylonitrile and/or siloxane.

Preferably, lithium-2-methoxy-1,1,2,2-tetrafluoro-ethanesulfonate is dissolved in the solvent. In preferred embodiments, the concentration of lithium-2-methoxy-1,1,2,2-tetrafluoro-ethanesulfonate in the electrolytes is in the range of 0.5 M to 2.5 M, more preferably in the range of 0.65 M to 2 M, most preferably in the range of 1 M to 1.5 M. Such a concentration of lithium-2-methoxy-1,1,2,2-tetrafluoro-ethanesulfonate may advantageously leads to good conductivity in the electrolytes.

Another subject matter of the disclosure relates to a lithium-based energy accumulator, preferably a lithium battery, lithium ion battery, lithium ion accumulator, lithium polymer battery or lithium ion condenser including lithium-2-methoxy-1,1,2,2-tetrafluoro-ethanesulfonate. Preferable likewise is a lithium-based energy accumulator, preferably a lithium battery, lithium ion battery, lithium ion accumulator, lithium polymer battery or lithium ion condenser comprising an electrolyte according to the disclosure, comprising lithium-2-methoxy-1,1,2,2-tetrafluoro-ethanesulfonate.

Lithium-based energy accumulators are suitable for all areas of use, particularly for larger systems such as automobiles, or as stationary energy storage for renewable energy.

Lithium-2-methoxy-1,1,2,2-tetrafluoro-ethanesulfonate can be produced by the normal methods of synthesis. Preferable is a method for producing lithium-2-methoxy-1,1,2,2-tetrafluoro-ethanesulfonate comprising the following steps:
a) conversion of difluorofluorosulfonylacetyl fluoride with triethylamine trihydrofluoride or trimethylammonium fluoride to triethylammonium-2-sufonyl fluoride-tetrafluoroethanolate or tetramethylammonium-2-sulfonyl fluoride-tetrafluoroethanolate,
b) methylation of triethylammonium-2-sufonyl fluoride-tetrafluoroethanolate or tetramethylammonium-2-sulfonyl fluoride-tetrafluoroethanolate to 2-methoxy-1,1,2,2-tetrafluoro-ethanesufonyl fluoride, and
c) conversion of 2-methoxy-1,1,2,2-tetrafluoro-ethanesufonyl fluoride with lithium hydroxide to lithium-2-methoxy-1,1,2,2-tetrafluoro-ethanesulfonate.

The synthesis of lithium-2-methoxy-1,1,2,2-tetrafluoro-ethanesulfonate takes place preferably proceeding from difluoro-fluorosulfonylacetyl fluoride. This is converted with triethylamine trihydrofluoride or tetramethylammonium fluoride. The reaction in dichloromethane or acetonitrile is preferred. The conversion of difluorosulfonylacetyl fluoride with triethylamine trihydrofluoride is carried out preferably in a mixture of triethylamine trihydrofluoride and triethylamine. A 1:2 mixture of triethylamine trihydrofluoride and triethylamine is preferred. The solvent is preferably dicholoromethane. The conversion of difluoro-fluorosulfonylacetylfluoride with the tetramethylammonium fluoride is carried out preferably in acetonitrile. In a preferred manner, triethylamine trihydrofluoride or tetramethylammonium fluoride is dissolved in the solvent, the mixture is cooled with liquid nitric acid, for example, and difluoro-fluorosulfonyl-acetylfluoride is condensed. Preferred temperatures for the conversion to triethylammonium-2-sulfonylfluoride-tetrafluoroethanolate or tetramethylammonium-2-sulfonyl fluoride-tetrafluoroethanolate are around 20° C.

Methylation of triethylammonium-2-sulfonylfluoride-tetrafluoroethanolate or tetramethyl-ammonium-2-sulfonyl-fluoride-tetrafluoroethanolate to 2-methoxy-1,1,2,2-tetrafluoroethane sulfonyl fluoride in step b) is carried out by means of a methylation agent selected from the group including dimethyl sulfate and/or trifluoromethane sulfonic acid ethyl ester (methyltriflate). In particular, methyltriflate is a strong methylation reagent. Preferably, triethylammonium-2-sulfonylfluoride-tetrafluoroethanolate is methylated by the use of dimethyl sulfate. Preferably, tetramethylammonium-2-sulfonylfluoride-tetrafluoroethanolate is methylated by the use of trifluoromethane sulfonic acid ethyl ester.

The conversion of 2-methoxy-1,1,2,2-tetrafluoroethane sulfonylfluoride with lithium hydroxide to lithium-2-methoxy-1,1,2,2-tetrafluoro-ethanesulfonate takes place preferably in methanol. As an example, lithium hydroxide is added during cooling to 0° C., and the reaction mixture reacts at a temperature in the range of 18° C. to 23° C.

Lithium-2-methoxy-1,1,2,2-tetrafluoro-ethanesulfonate is usable as a conductive salt in an electrolyte including an ionic liquid, for example, in lithium-based energy accumulators.

Ionic liquids are usable as non-aqueous electrolytes particularly for electrochemical uses, for example in batteries or electrochemical condensers, but also for electroplating, catalysis or chemical reactions. Ionic liquids with preferably wide electrochemical windows and low hygroscopy may therefore be advantageous not only for electrochemical uses.

Another subject matter of the disclosure relates to an ionic liquid having 2-methoxy-1,1,2,2-tetrafluoro-ethanesulfonate as anion and an organic cation selected from the group including alkylammonium, pyridinium, pyrazolium, pyrrolium, pyrrolinium, piperidinium, pyrrolidinium, imidazolium and/or sulfonium compounds.

Preferably, the cation is selected from the group including N-butyl-N-methylpyrrolidinium(PYR14), N-methyl-N-propylpyrrolidinium(PYR13), 1-ethyl-3-methylimidazolium (EMIM), 1-ethyl-2,3-dimethylimidazolium (EdiMIM) and or 1-butyl-3-methylimidazolium (BMIM).

Ionic liquids containing 2-methoxy-1,1,2,2-tetrafluoro-ethanesulfonate as anion and an organic cation can be useful to advantage in electrochemical applications, for example in combination with a lithium salt in lithium-based energy accumulators. Moreover, uses in solar cells or fuel cells may be advantageous. Ionic liquid containing fluorinated anions may also be usable advantageously as hydraulic fluid or inert fluid thinner for highly reactive chemicals.

BRIEF DESCRIPTION OF THE DRAWINGS

Examples and figures that serve as illustrations of the present disclosure are specified below.

The figures show in.

DETAILED DESCRIPTION

EXAMPLE 1

Figure 1:
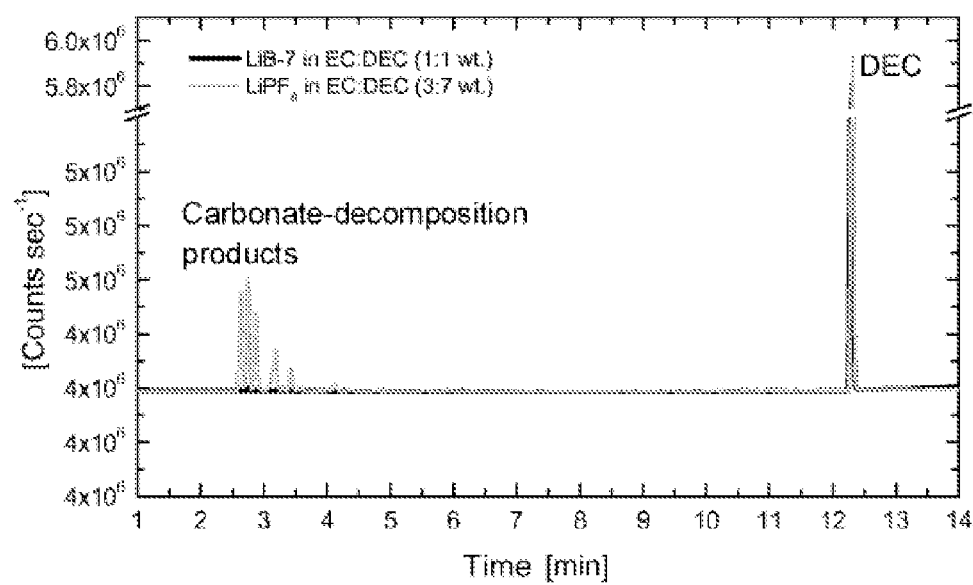
FIG. 1 The thermal stability of a 1 M lithium-2-methoxy-1,1,2,2-tetrafluoro-ethanesulfate (LiB-7) electrolyte solution in EC:DEC 1:1 in comparison with a 1 M solution of $LiPF_6$ in EC:DEC 1:1 after two-week storage at 95° C., specifically by means of GC-MS.

Production of lithium-2-methoxy-1,1,2,2-tetrafluoro-ethanesulfonate a) Production of triethylammonium-2-sulfonylfluoride-tetrafluoroethanolate:

21 mmol (2.12 g) triethylamine (ACROS, 99%) and 11 mmol triethylamine trihydrofluoride (ALDRICH, 98%) were dissolved in 20 ml dry dicholoromethane (ROTH). The solution was brought to −196° C. with liquid nitrogen and 32 mmol difluoro-fluorosulfonyl-acetylfluoride (Synquest, 99.8%) were condensed in. The reaction mixture was stirred for 3 hours at 20° C. Volatile parts were drawn off in vacuum. Triethylammonium-2-sulfonylfluoride-tetrafluoroethanolate as a yellowish oil was obtained.

b) Production of 2-Methoxy-1,1,2,2-tetrafluoro-ethanesulfonyl fluoride:

32 mmol of triethylammonium-2-sulfonylfluoride-tetrafluoroethanolate from step a) were dissolved in 20 ml dry 2-2'-dimethoxydiethylether (Diglyme, Aldrich). 39 mmol dimethyl sulfate (ACROS) were added slowly at 0° C. The reaction mixture was heated for 7 hours at 50° C. Then, the product was fractionally distilled under normal pressure. 2-methoxy-1,1,2,2-tetrafluoro-ethanesulfonyl fluoride as a colorless liquid was obtained.

c) Production of Lithium-2-methoxy-1,1,2,2-tetrafluoro-ethanesulfonate21:

mmol (3.78 g) 2-methoxy-1,1,2,2-tetrafluoro-ethanesulfonyl fluoride from step b) were dissolved in methanol (ROTH). A 2 n equivalent lithium hydroxide (ACROS, 98%) was added at 0° C. The suspension was stirred for 2 hours at room temperature. The suspension was centrifuged for 15 minutes, the liquid phase decanted and the solvent drawn off. The product was dried in vacuum for 6 hours at 60° C. Lithium-2-methoxy-1,1,2,2-tetrafluoro-ethanesulfonate was obtained in the form of white crystals.

EXAMPLE 2

Production of Lithium-2-methoxy-1,1,2,2-tetrafluoro-ethanesulfonate a) Production of Tetramethylammonium-2-sulfonylfluoride-tetrafluorosulfonate:

10 mmol of tetramethylammonium fluoride (99.9%) were dissolved in 20 ml dry acetonitrile (ROTH). The solution was brought to −196° C. with liquid nitrogen and 10 mmol difluoro-fluorosulfonyl-acetylfluoride were condensed in. The reaction mixture was stirred for 5 hours at 20° C. Volatile parts were drawn off in vacuum. The remaining solid matter was washed twice with 5 ml diethylether and dried in a vacuum. Tetramethylammonium-2-sulfonyl fluoride-tetrafluoroethanolate was obtained in the form of colorless crystals.

b) Production of 2-Methoxy-1,1,2,2-tetrafluoro-ethanesulfonyl fluoride:

20 mmol of tetramethylammonium-2-sulfonylfluoride-tetrafluoroethanolate from step a) were dissolved in 20 ml dry acetonitrile. 22 mmol trifluoromethane sulfonic acid methylester (methyltriflate) (ABCR, 98%) were added slowly at 0° C. The reaction mixture was stirred for 5 hours at room temperature. Then, the product was fractionally distilled under normal pressure. 2-methoxy-1,1,2,2-tetrafluoro-ethanesulfonyl fluoride as a colorless liquid was obtained.

c) Production of Lithium-2-methoxy-1,1,2,2-tetrafluoro-ethanesulfonate:

21 mmol (3.78 g) 2-methoxy-1,1,2,2-tetrafluoro-ethanesulfonyl fluoride from step b) were dissolved in methanol. A 2 n equivalent lithium hydroxide (ACROS, 98%) was added at 0° C. The suspension was stirred for 2 hours at room temperature. The suspension was centrifuged for 15 minutes, the liquid phase decanted and the solvent drawn off. The product was dried in vacuum for 6 hours at 60° C. Lithium-2-methoxy-1,1,2,2-tetrafluoro-ethanesulfonate was obtained in the form of white crystals.

EXAMPLE 3

Determination of Hydrogen Fluoride (HF) Development in Lithium-2-methoxy-1,1,2,2-tetrafluoro-ethanesulfonate-based Electrolytes in Comparison with $LiPF_6$ For the investigation of the HR-development in lithium-2-methoxy-1,1,2,2-tetrafluoro-ethane sulfonate-based electrolytes, the lithium-2-methoxy-1,1,2,2-tetrafluoro-ethanesulfonate produced according to Example 1 was dried for 24 hours with the aid of a turbomolecular pump (Pfeiffer Vacuum). During the process, the temperature was increased by 20° C. every 6 hours from 60° C. to 120° C. Then, the lithium-2-methoxy-1,1,2,2-tetrafluoro-ethanesulfonate was dissolved in a mixture of ethylene carbonate and diethyl carbonate (EC:DEC) (both by Ferro Corporation, battery grade) in the ratio 3:7 relative to parts by weight, so that a concentration of 1 M of lithium salt was obtained.

In an argon-filled glove box (Mbraun) ca. 400 μL of the 1 M lithium-2-methoxy-1,1,2,2-tetrafluoro-ethanesulfonate solution in EC:DEC was put into an glass NMR-tube and the NMR-tube was sealed by melting with a mini-blown torch under an absence of air. The sample was stored for 2 weeks at 95° C. (climate-controlled cabinet, Binder MK 53).

Parallelly, NMR-tubes were filled under identical conditions with 1 molar solutions of lithium-2-methoxy-1,1,2,2-tetrafluoro-ethanesulfonate in a mixture of ethylene carbonate and adiponitrile (Sigma-Aldrich, 99.9%) (EC:ADN) in the ratio 1:1 relative to parts by weight as well as $LiPF_6$ (Sigma-Aldrich, battery grade) in a mixture of ethylene carbonate and diethyl carbonate in the ratio 3:7 relative to parts by weight (EC:DEC, 3:7) and likewise stored for 2 weeks at 95° C.

Then, NMR spectra of protons and fluoride with the aid of an NMR AVANCE III spectrometer (200 MHz) by Bruker with a broadband sampling head (5 mm) were taken. An HF signal was not detected either in the protons or in the fluoride spectrum for the electrolytes of 1 M lithium-2-methoxy-1,1,2,2-tetrafluoro-ethanesulfonate in EC:DEC. The investigation of the thermal decomposition products of 1 M lithium-2-methoxy-1,1,2,2-tetrafluoro-ethanesulfonate in EC:ADN also showed no HF development, whereas it was detected for the $LiPF_6$-based electrolytes in the protons as well as in the fluoride spectrum as decomposition product.

EXAMPLE 4

Analysis of Thermal Stability in Comparison with $LiPF_6$

The decay products of a 1 M solution of lithium-2-methoxy-1,1,2,2-tetrafluoro-ethanesulfonate produced according to Example 1 in a mixture of 50 weight % ethylene carbonate and 50 weight % diethyl carbonate (EC:DEC, 1:1) were determined in contrast with the decay products of a 1 M solution of $LiPF_6$ in a mixture of 30 weight % ethylene carbonate and 70 weight % of diethyl carbonate (EC:DEC, 3:7) by means of GC-MS.

A 1 molar solution of lithium-2-methoxy-1,1,2,2-tetrafluoro-ethanesulfonate in EC:DEC (1:1) was filled into a polyether etherketone (PEEK) vessel inside a glove box with septum. For comparison, a 1 molar solution of $LiPF_6$ (Sigma-Aldrich, battery grade) in EC:DEC (3:7) was filled into a PEEK vessel. The vessels were then hermetically sealed and stored for 2 weeks at 95° C. The determination of decay products was carried out by a Clarus 600 gas chromatograph (Perkin Elmer) connected to a Clarus 600 mass spectrometer (Perkin Elmer).

FIG. 1 shows the decay products of the thermal aging at 95° C. As FIG. 1 shows, the decay products in the case of the $LiPF_6$ electrolytes were to be determined. For the 1 M LiPF6 electrolytes in EC:DEC between 2.5 min and 3.5 min carbonate decay products were detected by means of the signal. The lithium-2-methoxy-1,1,2,2-tetrafluoro-ethanesulfonate, however, shows no carbonate decay products after two-week storage at 95° C. The signal after 12 min. is to be assigned to diethyl carbonate.

This result confirms the thermal stability of the electrolyte containing lithium-2-methoxy-1,1,2,2-tetrafluoro-ethanesulfonate.

EXAMPLE 5

Determination of Conductivity of Lithium-2-methoxy-1,1,2,2-tetrafluoro-ethanesulfonate The conductivity of lithium-2-methoxy-1,1,2,2-tetrafluoro-ethanesulfonate was determined in different solvents in a temperature range of −40° C. to +60° C.

The lithium-2-methoxy-1,1,2,2-tetrafluoro-ethanesulfonate produced according to Example 1 was dried for 24 hours with the aid of a turbomolecular pump (Pfeiffer Vacuum). The temperature was increased during the process 20° C. every 6 hours from 60° C. to 120° C. Mixtures of 50 weight % of ethylene carbonate (EC) (Ferro Corporation, battery grade) and 50 weight % of diethyl carbonate (DEC) (Ferro Corporation, battery grade), dimethyl carbonate (DMC) (Ferro Corporation, battery grade) or adiponitrile (ADN) (Sigma-Aldrich, 99.9%), respectively, were presented. The respectively required amounts of lithium-2-methoxy-1,1,2,2-tetrafluoro-ethanesulfonate were dissolved into these solvent mixtures, so they yielded a concentration of 1 M of lithium salt.

The conductivity of the electrolyte was investigated by the use of platinum conductivity measuring cells (Amel Glassware, cell constant 1 $cm^{-1}$) with a potentiostat (Solartron 1280A) in connection with an impedance measuring unit (Solartron 1260) in a temperature range of −40° C. to +60° C. (Climate-Controlled Cabinet, Binder MK53). The conductivity measuring cells were first warmed at 60° C. and then cooled in steps of 5° C. to −40° C.

Figure 2:
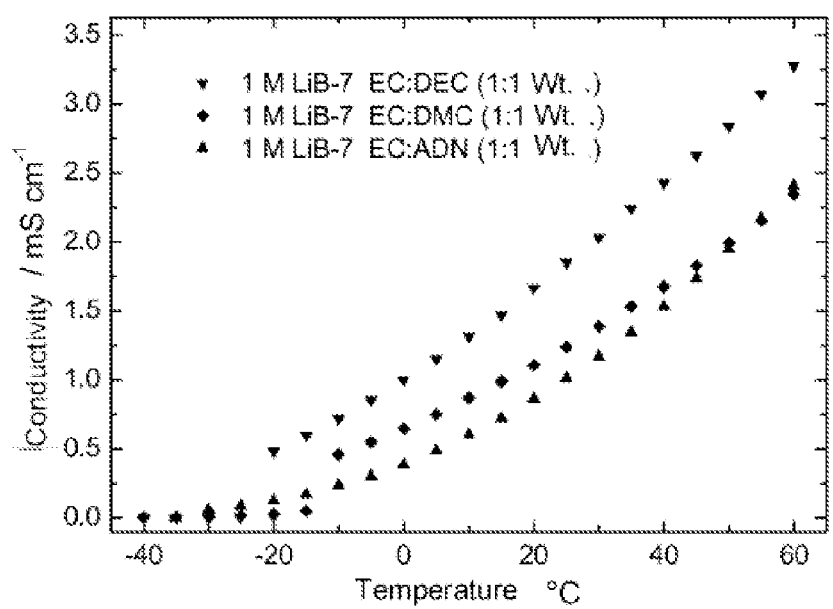
FIG. 2 The temperature-dependent conductivity of lithium-2-methoxy-1,1,2,2 tetrafluoro-ethanesulfate (LiB-7) in various solvent mixtures.

As shown in FIG. 2, the highest conductivity was reached in the temperature range of −20° C. to +60° C. in the solvent mixture EC:DEC 1:1. The conductivities for the different solvent mixtures at 20° C. were 1.67 mS $cm^{-1}$ for a 1:1 mixture of ethylene carbonate and diethyl carbonate, 1.1 mS $cm^{-1}$ for a 1:1 mixture of ethylene carbonate and dimethyl carbonate (EC:DMC 1:1) and 0.86 mS $cm^{-1}$ for a 1:1 mixture of ethylene carbonate and adiponitrile (EC:ADN 1:1).

This shows that lithium-2-methoxy-1,1,2,2-tetrafluoro-ethanesulfonate in the common carbonate solvents have a sufficient conductivity at 20° C.

EXAMPLE 6

Determination of the Electrochemical Stability of Lithium-2-methoxy-1,1,2,2-tetrafluoro-ethanesulfonate Electrochemical stability of a 1 M solution of lithium-2-methoxy-1,1,2,2-tetrafluoro-ethanesulfonate in a mixture of ethylene carbonate and diethyl carbonate in the ratio 1:1 relative to parts by weight (EC:DEC, 1:1) in contrast to the stability of a 1 M solution of $LiPF_6$ (Sigma-Aldrich, battery grade) in a mixture of ethylene carbonate and diethyl carbonate in the ratio 3:7 relative to parts by weight (EC:DEC, 3:7) was determined by means of so-called linear sweep voltammetry (LSV). A continuous change of electrode tension (linear sweep) occurs in this method. For this, lithium-2-methoxy-1,1,2,2-tetrafluoro-ethanesulfonate produced according to Example 1 was dried for 24 hours with the aid of a turbomolecular pump (Pfeiffer vacuum), during which the temperature was increased by 20° C. from 60° C. to 120° C.

The experiments were carried out in a 3-electrode arrangement in modified Swagelok® T pieces (tube connectors, stainless steel parts) with a platinum electrode (eDAQ, model ET075, 1 mm diameter) as work electrode and lithium foil (12 mm or 7 mm diameter, Chemetall) as contrast and reference electrode. The cell body was lined with polyester foil siliconized on one side (Mylar®, PPI-SP 914, 100 μm), and the electrodes were inserted into the cell body. The electrodes were separated with fleece (Freudenberg®, FS2226E, 6 layers) that was soaked with the corresponding electrolytes. The feed rate was 1 mV $s^{-1}$.

As cathodic stability limit, the potential at which a reduction starts, was defined as that potential at which the current density is less than −0.1 mA $cm^{-2}$ and as anodic stability limit, the potential at which oxidation starts, that potential at which the current density is more than +0.1 mA $cm^{-2}$. In particular, the anodic stability is dependent on the stability of the electrolytes used.

Figure 3:
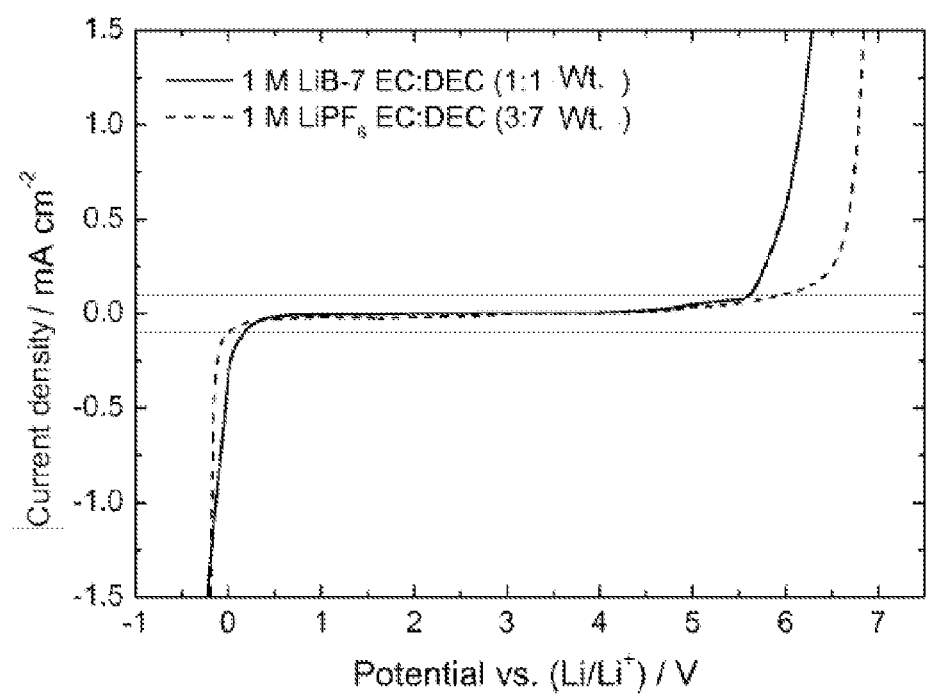
FIG. 3 The electrochemical stability window of lithium-2-methoxy-1,1,2,2-tetrafluoro-ethanesulfonate (LiB-7) in EC:DEC 1:1, and $LiPF_6$, in EC:DEC 3:7.

As shown in FIG. 3, the cathodic stability reached 0.2 V with the electrolyte lithium-2-methoxy-1,1,2,2-tetrafluoro-ethanesulfonate in EC:DEC 1:1, 0.0 V with $LiPF_6$ in EC:DEC 3:7. The anodic stability of lithium-2-methoxy-1,1,2,2-tetrafluoro-ethanesulfonate in EC:DEC 1:1 was at 5.6 V, only slightly less by 0.3 V than that of $LiPF_6$ in EC:DEC 3:7. This anodic stability is fully sufficient for the use of the electrolytes in combination with high voltage cathode materials.

This result shows that lithium-2-methoxy-1,1,2,2-tetrafluoro-ethanesulfonate in the usual carbonate solvents has a sufficiently good electrochemical stability for all electrochemical uses.

EXAMPLE 7

Determination of the Corrosion Behavior of Lithium-2-methoxy-1,1,2,2-tetrafluoro-ethanesulfonate The corrosion behavior of lithium-2-methoxy-1,1,2,2-tetrafluoro-ethanesulfonate in relation to aluminum was determined in comparison with lithium bis(trifluoromethane sulfonyl)imide (LiTFSI), known to be corrosive. Aluminum is used on the cathode side as a current collector and is in the potential range in which lithium ion batteries operate and thermodynamically unstable. It is therefore suitable that the electrolyte be in the position to form a protective layer on aluminum that prevents corrosion of the current collector. With electrolytes that are not in the position to form a protective layer on aluminum, like LiTFSI, the current density rises because of aluminum corrosion during the potentiostatic step, whereas it diminishes when no aluminum corrosion takes place.

A 1 M solution of lithium-2-methoxy-1,1,2,2-tetrafluoro-ethanesulfonate, LiPF6 and LiTFSI were used in a mixture of ethylene carbonate and diethyl carbonate in the ratio 3:7 relative to parts by weight (EC:DEC, 3:7). Beforehand, the lithium-2-methoxy-1,1,2,2-tetrafluoro-ethanesulfonate produced according to Example 1 was dried for 24 hours with the aid of a turbomolecular pump (Pfeiffer vacuum), during which the temperature is increased 20° C. every 6 hours from 60° C. to 120° C.

For measurement of the aluminum corrosion properties of the electrolytes 3 electrode cells (modified Swagelok® T pieces, high-grade steel parts) were produced with aluminum foil as work electrode and lithium foil (12 mm or 7 mm diameter, Chemetall) as contrast and reference electrode carried out. The cell body was lined with polyester foil siliconized on one side (Mylar®, PPI-SP 914, 100 µm), and the electrodes were inserted into the cell body. The electrodes were separated with fleece (Freudenberg®, FS2226E, 6 layers) that was soaked with the corresponding electrolytes.

Starting with the open-circuit voltage of the cell, the potential was increased in 100 mV steps by 1 mVs$^{-1}$ and then the respective potential was held for one hour. The progress of the current density during this so-called potentiostatic step at 4.5 V is represented in FIG. 4.

Figure 4:
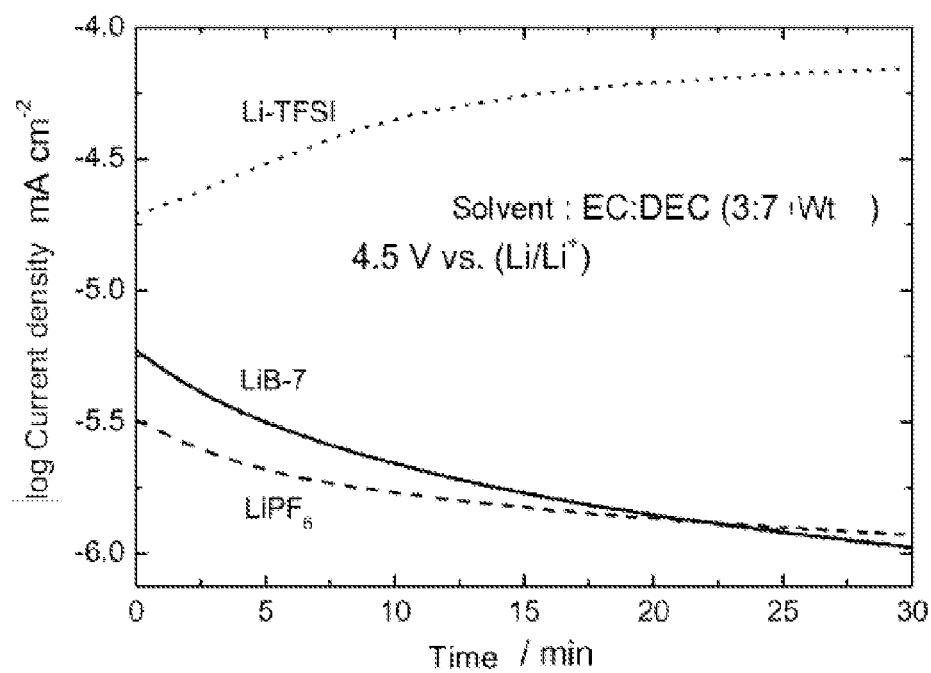
FIG. 4 Corrosion measurements on aluminum foil with lithium-2-methoxy-1,1,2,2-tetrafluoro-ethanesulfonate (LiB-7), $LiPF_6$ and lithium bis(trifluoro-methanesulfonyl) imide in EC:DEC 3:7.

As shown in FIG. 4, the current density rose at a potential of 4.5 V vs. Li/Li$^+$ with the use of LiTFSI as conductive salt. This effect is to be attributed to aluminum corrosion. On the other hand, the current density decreased in the measurement of the electrolytes based on lithium-2-methoxy-1,1,2,2-tetrafluoro-ethanesulfonate and LiPF$_6$.

This result shows that the lithium-2-methoxy-1,1,2,2-tetrafluoro-ethanesulfonate electrolyte, like the LiPF$_6$ electrolyte, is capable of preventing corrosion of aluminum by the formation of a protective layer at a potential of 4.5 V.

EXAMPLE 8

Determination of the Cyclization Behavior of Lithium-2-methoxy-1,1,2,2-tetrafluoro-ethanesulfonate The cyclization behavior of a 1 M solution of lithium-2-methoxy-1,1,2,2-tetrafluoro-ethanesulfonate in a mixture of ethylene carbonate and diethyl carbonate in the ratio 1:1 relative to parts by weight was determined in comparison to the standard electrolytes of a 1 M solution of LiPF$_6$ in a mixture of ethylene carbonate and diethyl carbonate in the ratio 3:7 relative to parts by weight. Beforehand, the lithium-2-methoxy-1,1,2,2-tetrafluoro-ethanesulfonate produced according to Example 1 was dried for 24 hours with the aid of a turbomolecular pump (Pfeiffer vacuum), during which the temperature was increased 20° C. every 6 hours from 60° C. to 120° C.

Three electrode cells (modified Swagelok® T pieces, stainless steel parts) with Timrex T44 graphite (TIMCAL Graphite&Carbon, 12 mm diameter) as anode, an ~8-fold capacitative overdimensioned NCA cathode (lithium-nickel-cobalt-aluminum-oxide, Li(Ni$_{0.8}$Co$_{0.15}$Al$_{0.05}$)O$_2$, 12 mm diameter) as lithium source and lithium metal (7 mm diameter, Chemetall) as reference electrodes are produced. The cell body was lined with polyester foil siliconized on one side (Mylar®, PPI-SP 914, 100 µm) and the electrodes were inserted into the cell body. The electrodes were separated with fleece (Freudenberg®, FS2226E, 6 layers) that was soaked with the corresponding electrolytes. The cells were first formed for 3 cycles with a rate of C/5 and then charged and discharged for 20 cycles in a potential range of 0.025 V-1.5 V at 1 C.

In charging, the cells, after reaching the charge voltage, were respectively further charged at a constant voltage (25 mV) for an hour. Then, a so-called C-rate test was carried out in which each was charged with a C-rate of C/2 and then an hour of constant voltage (25 mV) and at various C-rates, from C/5 to 5 C, discharged. After the C-rate test, the cells were charged and discharged for 5 cycles with C/5 and then for 30 cycles with 1 C. In charging, as before, a constant voltage step of one hour was carried out for each.

Figure 5A:
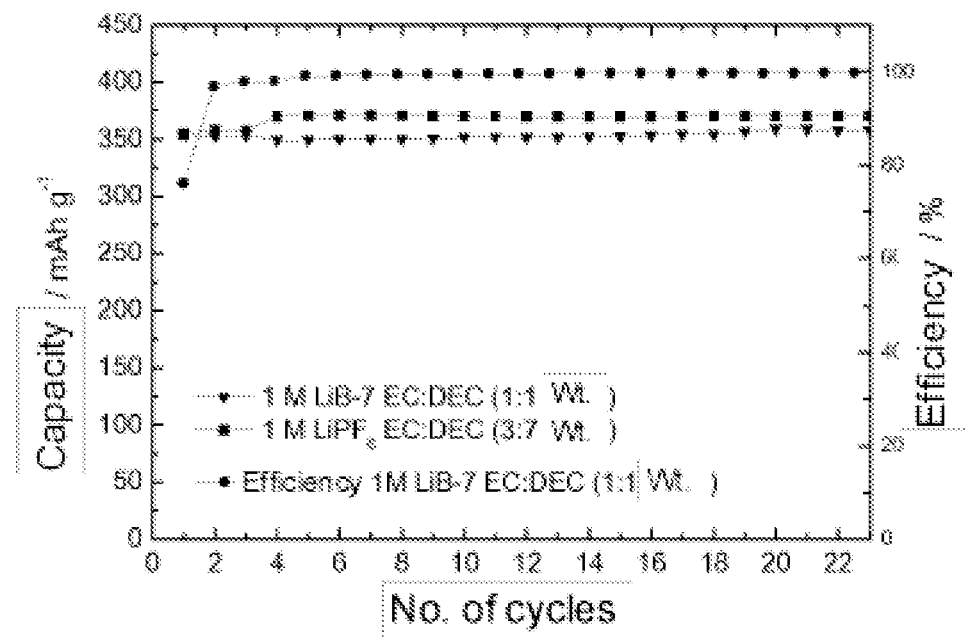
FIG. 5 A constant current cycling of Graphite NCA Swagelok® cells charged with a C-rate of 1 C and an hour of constant voltage and discharged with a C-rate of 1 C (FIG. 5A); C-rates test (FIG. 5B); constant current cycling according to C-rates test (FIG. 5C).

As FIG. 5A shows, the cell with electrolyte 1 M lithium-2-methoxy-1,1,2,2-tetrafluoro-ethanesulfonate in EC:DEC 1:1 had an initial capacity of ca. 350 mAh g$^{-1}$ after the forming of the cell, that continuously rose with the number of cycles to ca. 360 mAh g$^{-1}$ in the 20th cycle. This shows that there is an improvement of the moistening of the electrodes with rising cycle number. The cells with the electrolytes LiPF$_6$ reached the theoretical capacity of ca. 370 mAh g$^{-1}$ after the 3rd forming cycle.

Figure 5B:
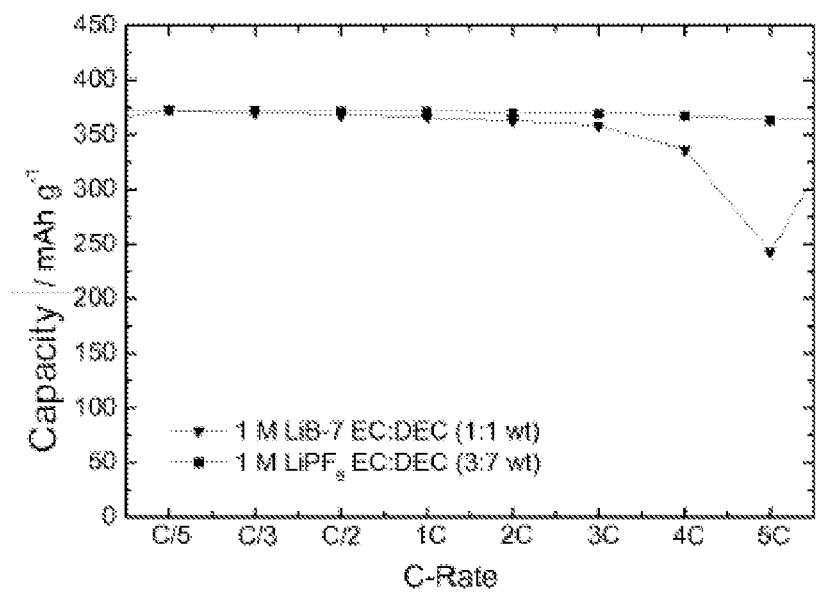
Figure 5C:
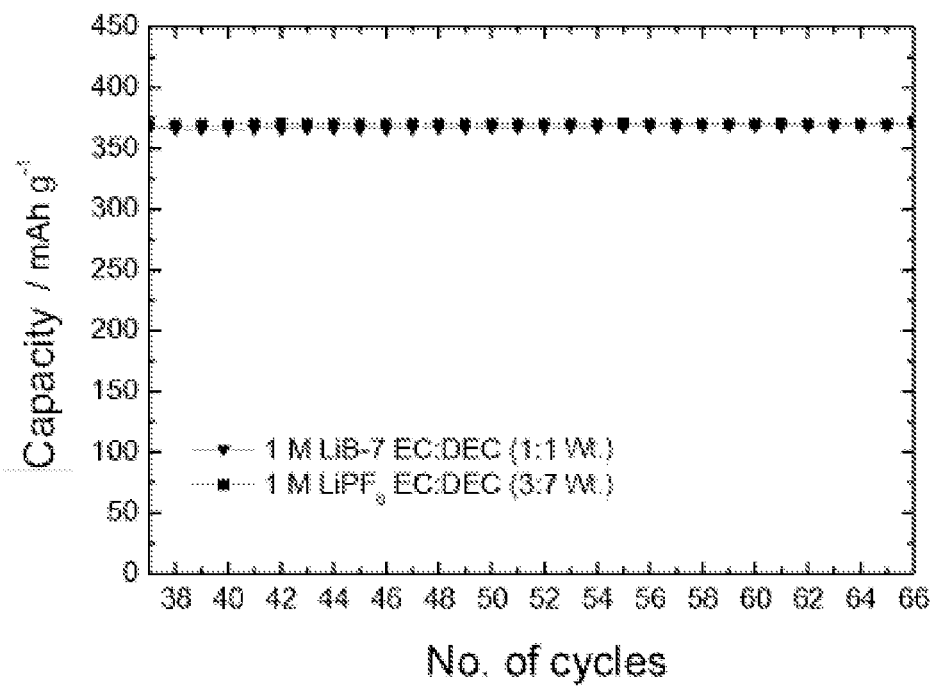

As shown in FIG. 5B, in the C-rates test both cells showed up to a C-rate of 2 C comparable capacities with a difference of less than 10 mAh g$^{-1}$. Only after a high C-rate of >3 C were there significant capacity differences. This is attributed to the lower conductivity of 1 M lithium-2-methoxy-1,1,2,2-tetrafluoro-ethanesulfonate in EC:DEC 1:1 of 1.7 mS cm$^{-1}$ (20° C.) in comparison with ca. 6.5 mS cm$^{-1}$ (20° C.) for 1 M LiPF$_6$ in EC:DEC 3:7. As shown in FIG. 5C, after the C-rate test and 5 cycles at C/5, even the cell with 1 M lithium-2-methoxy-1,1,2,2-tetrafluoro-ethanesulfonate in EC:DEC 1:1 reached the theoretical capacity and had excellent cycle stability over 30 cycles.

The results show that electrolytes with lithium-2-methoxy-1,1,2,2-tetrafluoro-ethanesulfonate as conductive salt had a somewhat lower conductivity and oxidation stability in comparison with electrolytes with the standard salt LiPF$_6$, but had an excellent cycle stability and no HF development after thermal aging at 95° C.

These results show that lithium-2-methoxy-1,1,2,2-tetrafluoro-ethanesulfonate presents a possibility to replace LiPF$_6$ as a conductive salt in lithium ion batteries.

The invention claimed is:
1. Lithium-2-methoxy-1,1,2,2-tetrafluoro-ethanesulfonate.
2. An electrolyte for a lithium-based energy accumulator including lithium-2-methoxy-1,1,2,2-tetrafluoro-ethanesulfonate.
3. The electrolyte of claim 2 characterized in that the electrolyte contains an aprotic solvent, an ionic liquid and/or a polymer matrix.
4. The electrolyte of claim 3 characterized in that the aprotic solvent is selected from the group including ethylene carbonate, propylene carbonate, diethyl carbonate, dimethyl carbonate, ethyl methyl carbonate, acetonitrile, glutaronitrile, adiponitrile, pimelonitrile, γ-butyrolactone, γ-valerolactone, dimethoxyethane, 1,3-dioxalane, methyl acetate and/or mixtures thereof.
5. The electrolyte of claim 3 characterized in that the aprotic solvent comprises a mixture of ethylene carbonate and at least one other aprotic solvent, preferably diethyl carbonate, preferably in the ratio in the range of ≥1:9 to ≤9:1, more preferably in the range of ≥3:7 to ≤7:3, most preferably in the range of ≥3:7 to ≤1:1.
6. The electrolyte of claim 2 characterized in that the concentration of lithium-2-methoxy-1,1,2,2-tetrafluoro-ethanesulfonate in the electrolytes lies in the range of ≥0.5 M to ≤2.5 M, more preferably in the range of ≥0.65 M to ≤2 M, most preferably in the range of ≥1 M to ≤1.5 M.

7. A lithium battery, lithium ion battery, lithium ion accumulator, lithium polymer battery or lithium ion condenser including lithium-2-methoxy-1,1,2,2-tetrafluoro-ethanesulfonate.

8. A method of producing lithium-2-methoxy-1,1,2,2-tetrafluoro-ethanesulfonate, the method comprising the following steps:
   a) conversion of difluorosulfonyl acetyl fluoride with triethylamine trihydrofluoride or tetramethylammonium fluoride to triethylammonium-2sulfonylfluoride-tetrafluoro-ethanolate or tetramethylammonium-2-sulfonylfluoride-tetrafluoro-ethanolate,
   b) methylation of triethylammonium-2-sulfonylfluoride-tetrafluoro-ethanolate or tetramethylammonium-2-sulfonylfluoride-tetrafluoro-ethanolate to 2-methoxy-1,1,2,2-tetrafluoro-ethanesulfonyl fluoride, and
   c) conversion of 2-methoxy-1,1,2,2-tetrafluoro-ethanesulfonyl fluoride with lithium hydroxide to lithium-2-methoxy-1,1,2,2-tetarfluoro-ethanesulfonate.

9. An ionic liquid including 2-methoxy-1,1,2,2-tetrafluoro-ethanesulfonate as anion and an organic cation selected from the group including alkyl ammonium, pyridinium, pyrazolium, pyrrolium, pyrrolinium, piperidinium, pyrrolidinium, imidazolium and/or sulfonium compounds, wherein the cation is selected from the group including N-butyl-N-methylpyrrolidinium, N-methyl-N-propylpyrrolidinium, 1-ethyl-3-methylimidazolium, 1-ethyl-2,3-dimethylimidazolium and/or 1-butyl-3-imidazolium.

\* \* \* \* \*